Figure 1:
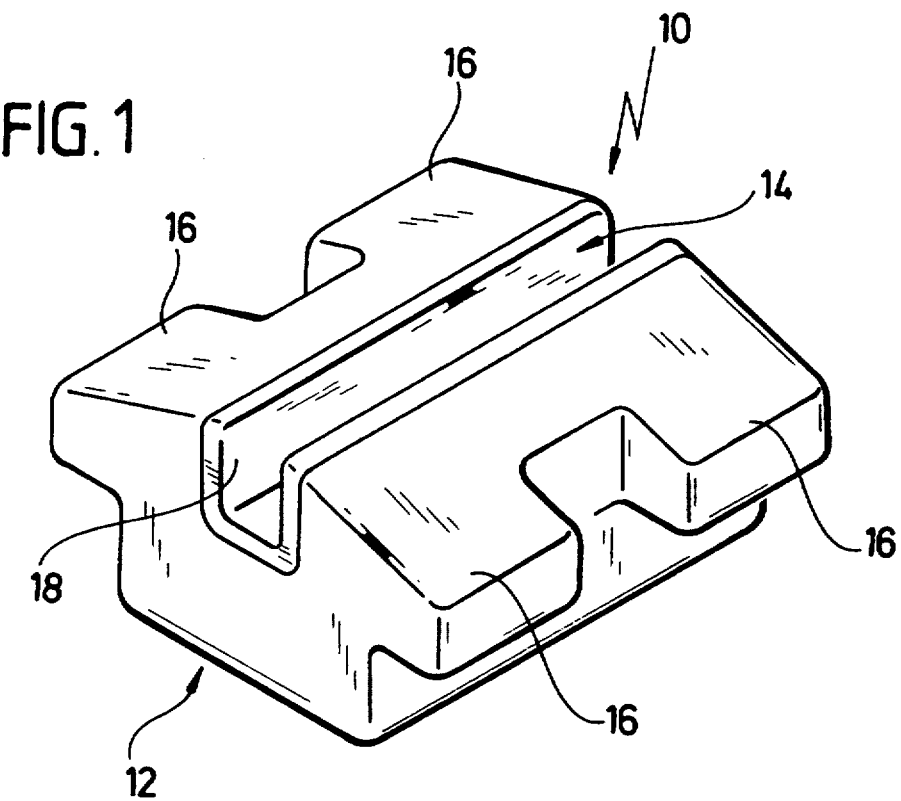

United States Patent [19]

Sernetz

[11] Patent Number: 5,429,499
[45] Date of Patent: Jul. 4, 1995

[54] ORTHODONTIC AID

[75] Inventor: Friedrich Sernetz, Pforzheim, Germany

[73] Assignee: Dentaurum J.P. Winkelstroeter KG, Inspringen, Germany

[21] Appl. No.: 81,245

[22] PCT Filed: Oct. 15, 1992

[86] PCT No.: PCT/EP92/02382

§ 371 Date: Aug. 10, 1993

§ 102(e) Date: Aug. 10, 1993

[87] PCT Pub. No.: WO93/07830

PCT Pub. Date: Apr. 29, 1993

[30] Foreign Application Priority Data

Oct. 26, 1991 [DE] Germany ............... 41 35 434.6

[51] Int. Cl.⁶ ................................................. A61C 7/00
[52] U.S. Cl. ................................................. 433/8
[58] Field of Search ............................... 433/8, 9, 16

[56] References Cited

U.S. PATENT DOCUMENTS

| | | | |
|---|---|---|---|
| 3,847,865 | 11/1974 | Duggins | 260/42.52 |
| 3,930,311 | 1/1976 | Andrews | 433/8 |
| 3,964,165 | 6/1976 | Stahl | 433/8 |
| 4,107,844 | 8/1978 | Kurz | 433/8 |
| 4,251,576 | 2/1981 | Osborn et al. | 428/331 |
| 4,299,569 | 11/1981 | Frantz | 433/8 |
| 4,302,532 | 11/1981 | Wallshein | 433/8 |
| 4,988,293 | 1/1991 | Collins et al. | 433/8 |
| 5,064,369 | 11/1991 | Kawaguchi | 433/8 |
| 5,078,596 | 1/1992 | Carberry et al. | 433/8 |
| 5,254,002 | 10/1993 | Reher et al. | 433/8 |

FOREIGN PATENT DOCUMENTS 0161831 4/1985 European Pat. Off. .

Primary Examiner—Cary E. O'Connor
Attorney, Agent, or Firm—Leydig, Voit & Mayer, Ltd.

[57] ABSTRACT

In order to improve the mechanical strength of an orthodontic aid produced on a plastics basis, without having to tolerate any appreciable reduction in the transparency of the bracket, it is suggested that a reinforcement increasing the mechanical strength be arranged at least in those areas acted upon by tooth correction forces, this reinforcement being produced with the use of a ceramic material.

16 Claims, 1 Drawing Sheet

ORTHODONTIC AID

The invention relates to an orthodontic aid, bracket or buccal tube, produced on a plastics basis, comprising a reinforcement increasing the mechanical strength and arranged at least in areas acted upon by tooth correction forces.

Up to now, orthodontic aids, e.g. brackets or buccal tubes made of metal, plastics or ceramics have been known which all have their differing advantages and disadvantages. Aids made of plastics are inexpensive and easy to produce and simple to attach to and remove from the surfaces of the patient's teeth. A disadvantage of these aids is the fact that they are pliable in the areas, in which they are acted upon by tooth correction forces, and so they do not allow any exact control of the tooth displacement to be carried out.

Metallic, orthodontic aids have the disadvantage that the aids are very conspicuous due to the metallic gleam of the parts and their silvery colour and they give the patient undergoing treatment a so-called "metallic smile".

Ceramic parts, in particular produced from alumina, are considerably less conspicuous in the mouth of the patient than the metallic brackets. They do, however, have the disadvantage that they are very hard and pose problems during removal from the surface of the teeth after successful treatment.

In order to at least partially obviate the problems with the brackets produced on a plastics basis, it has already been suggested that these be provided with a metal insert in order to improve the stiffness of the bracket and also its mechanical strength. The metallic inserts do, however, cause a reduction in the transparency of the bracket and so this is just as noticeable in the mouth of the patient as metallic brackets. Moreover, when the metallic inserts lie exposed on the surface of the aid, they exhibit, in the same way as the metallic brackets, too great an abrasion and too great a friction with the arch wires generating the correction forces.

The object of the invention is to avoid the aforesaid disadvantages in an orthodontic aid of the type described at the outset.

This object is accomplished in accordance with the invention, in a bracket of the type described at the outset, in that the reinforcement is produced with the use of a ceramic material.

Despite the extremely large differences in the heat expansion and in the modulus of elasticity of conventional plastics and ceramic materials, surprisingly no problems arise at the transitions between materials. This is especially unexpected since, when the aids are worn in the mouth of the patient, a vast number of hot-cold cycles occur daily, for example when drinking hot or cold beverages or consuming hot meals or ice cream.

Oxide ceramic material is particularly suitable. In this respect, two solutions are in principle conceivable, namely, on the one hand, the use of the ceramic material as filler for the plastic of the plastic bracket in the mechanically stressed parts or, on the other hand, its use as starting product for the manufacture of an insert element for the mechanically stressed parts of the bracket.

The use of the oxide inorganic masses in the production of the reinforcement (in the following generally referred to as ceramics) reduces the abrasion and diminishes the friction of the arch wire inserted in the slot of a bracket. Preferably, the reinforcement essentially forms the surface regions of the aid which are acted upon by the correction forces.

The ceramic mass may be produced transparent or at least opaque and, for this reason, the aesthetic requirements to be met by the orthodontic aids are better fulfilled. Normally, a difference in colour to the plastic material can scarcely be ascertained. In comparison with the brackets which consist completely of ceramics, the risk of breakage during the removal of the bracket from the patient's tooth is avoided, and also the problems involved with the bonding of the ceramic brackets to the tooth surface, since the inventive orthodontic aids, like the known aids which consist altogether of plastic and are not reinforced, can be attached and removed in a known manner.

The reinforcement preferably comprises a ceramic part, in particular made of sintered, polycrystalline alumina. In the case of this material, the transparency or translucency of the part, in particular, can be adapted very well to the transparency or translucency of the surrounding plastic material. The plastic material is preferably adapted in its colour, and therefore the reinforcement part as well, to the colour of the teeth, possibly even individually to the colour of the teeth of the particular patient.

The ceramic part of the reinforcement can be held in a force fit in the aid, whereby the aid and the reinforcement part are then produced separately and not joined together until a further operating process.

The actual aid part can just as easily be sprayed onto a prefabricated ceramic reinforcement part. However, the reinforcement part can, of course, also be bonded to the plastic aid.

Alternatively to a ceramic part, the reinforcement can be a polymer part filled with particulate ceramic material. This can be produced independently of the orthodontic aid or be designed in one piece with it. The separately produced reinforcement can, again, be held in a force fit in the orthodontic aid or be bonded thereto. It is also possible in this case for the aid to be sprayed onto the reinforcement.

Preferably, the plastic, from which the orthodontic aids are made, will comprise a polyethylene, polyester, polycarbonate or polyacrylic resin portion or copolymer portions derived herefrom.

The particulate, ceramic material for reinforcing the polymer parts will preferably comprise essentially $ZrO_2$ or silicon dioxide, in particular in the form of powdered quartz or cristobalite, or even alumina, especially in its trihydrate form.

Alumina trihydrate has the advantage over silicon dioxide that it is less hard and therefore no metal abrasion, for example from the arch wire, takes place, i.e. metal parts rubbing on the reinforcement parts do not lead to so-called writing traces which can give the part a grey or dull and therefore conspicuous appearance.

The average particle size of the filler material is preferably selected to be in the range of between 5 $\mu$m to 100 $\mu$m since, on the one hand, the particles of this size can easily be stabilized in the mixture provided for the manufacture of the reinforcement part and, on the other hand, an adequate surface smoothness of the produced reinforcement part is ensured. The proportion of the ceramic material in the overall mass can be very high, i.e. 50–80% by weight.

A bracket, which is equipped with a base for direct bonding of the aid to a surface of a tooth, can, in particular, be considered as a reinforced, orthodontic aid. The reinforcement is then designed such that the strength of the base is essentially not influenced. This limitation of the reinforcement parts to the areas of the bracket receiving the forces is important, in particular, with a view to the later removal of the brackets from the tooth surface since, in the case of the otherwise flexible plastic brackets, a gradual separation of the bracket base from the point of bonding on the tooth surface may be carried out. The forces which act on the tooth at any point of time hereby remain so slight that no tears can occur in the tooth enamel on the tooth surface.

The removal of the brackets from the tooth surface can be carried out with simple pliers-type instruments, as already known from previous plastic brackets.

The reinforcement of the bracket is limited, in particular, to that region of the slot provided for accommodating an arch wire, via which the correction forces of the arch wire are transferred to the bracket and, finally, to the tooth.

An additional, alternative embodiment of the invention consists in the fact that the aid, in particular the bracket, is produced altogether from a plastic filled to a considerable extent with particulate ceramic material. In this case, as in the variant described in the above, the production method as well as the selection of material for the highly filled plastics is known from the field of sanitation technology. For example, DE-PS 24 49 656 and U.S. Pat. No. 3,847,865 are cited.

Although sanitation technology deals with a quite different set of problems to those of orthodontic aids, the material described in this case can surprisingly and advantageously be used, modified if necessary, in orthodontics. It is particularly surprising to find that the material which is known in sanitation technology only for objects having large surfaces, such as e.g. baths or also kitchen worktops, can be utilized without problem for the production of very small and relatively complex structures.

Figure 2:
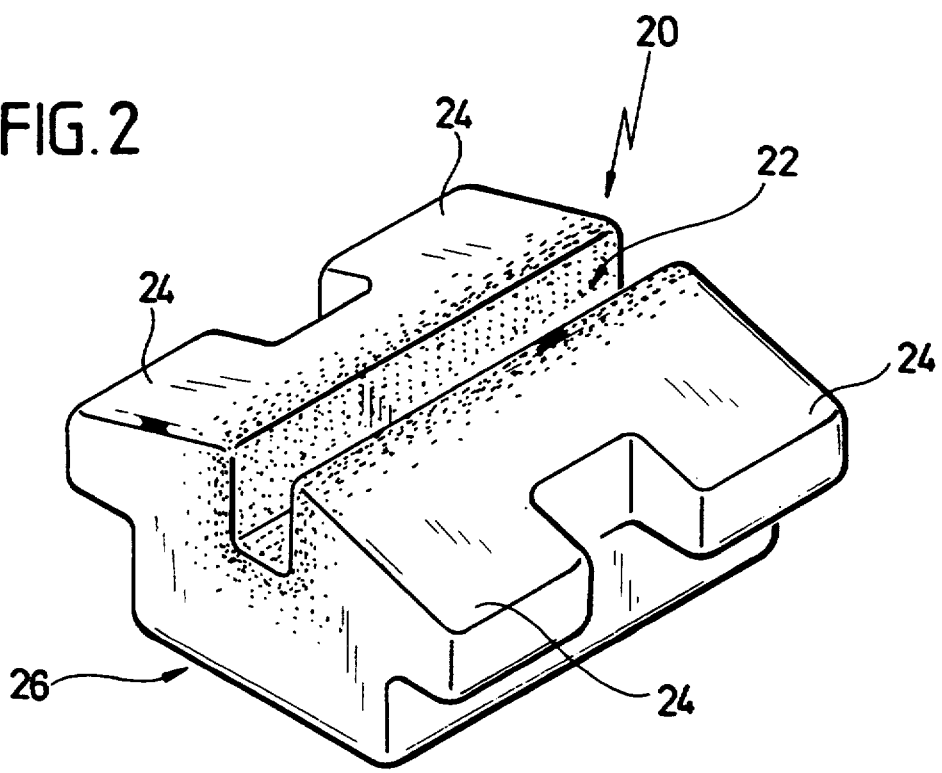

These and additional advantages of the invention are explained in greater detail in the following on the basis of the drawings. These drawings show in detail, in FIG. 1 an inventive orthodontic aid in the form of a bracket having an inserted reinforcement;

FIG. 2 an inventive orthodontic aid in the form of a bracket having an integrally designed reinforcement.

FIG. 1 shows an orthodontic aid in the form of a bracket and designated as a whole with the reference numeral 10. This is customarily used in orthodontics for performing corrections to the position of teeth.

The bracket has an underside or base 12, with which it can be bonded to a surface of a tooth.

A slot 14, which is essentially rectangular in cross section, is provided in the longitudinal direction and on the upper side. An arch wire, which applies the correction forces for altering the position of teeth to the bracket, is inserted into this slot.

In addition, so-called tie wings 16 are provided on both sides of the slot 14 and these form a support for attachment means for the arch wire. The arch wire can be held securely in the slot 14 with the attachment means and this ensures over the treatment period that the correction forces always act on the tooth in the manner desired by the dentist in charge.

The special inventive characteristic of the bracket 10 illustrated in FIG. 1 is to be seen in the reinforcement of the bracket in the region of the slot 14, whereby in the embodiment shown in FIG. 1 a reinforcement part 18 is inserted which extends over the entire length of the slot 14. Alternatively, it is possible for the reinforcement part 18 to be designed somewhat shorter than the slot 14 and be covered at its end faces by the plastic material of the remaining bracket body. The reinforcement part 18 consists, in this case, of sintered, polycrystalline alumina and has very similar colour and translucency values to the surrounding plastic material of the bracket 10.

The bracket, when attached to the tooth, differs in its appearance only insignificantly from the purely plastic brackets, i.e. it remains essentially invisible when worn by the patient. Nevertheless, a considerable improvement in the accuracy of the tooth correction achieved is obtained with the inventive bracket since the correction forces are transferred over considerably larger surfaces to the bracket body due to the insert of the reinforcement part 18 in the bracket 10, without any deformation of the slot 14 hereby resulting.

In the embodiment shown in FIG. 1, the side walls of the reinforcement part 18 reach as far as the upper side of the bracket 10. Alternatively to this, it would also be possible to design the side walls to be somewhat lower, whereby they are then covered in the region of the upper side of the bracket by the plastic material of the bracket body. It is important for the reinforcement part 18, with a view to minimizing the friction between arch wire and bracket in the region of the slot 14, that those surface regions of the slot 14, which come into contact with the arch wire and via which the correction forces for the teeth are conveyed from the arch wire onto the bracket, are formed by the reinforcement part 18.

FIG. 2 shows an alternative embodiment of the invention, also on the basis of a bracket 20, whereby, as in the bracket described in FIG. 1, a slot 22 is provided for receiving an arch wire, which is not shown, as well as so-called tie wings 24 which serve to fix the arch wire in position in the slot 22. The bracket is, like the bracket of FIG. 1, bonded with its underside or base 26 to the tooth surface of the teeth of the patient undergoing treatment.

In contrast to the embodiment of FIG. 1, the slot 22 is, however, not lined with a separate reinforcement part but rather the plastic material of the bracket 20 is mechanically reinforced by the introduction in certain areas of inorganic, oxide material, in particular alumina in its trihydrate form, to such an extent that it has, with respect to the transfer of correction forces from the arch wire to the bracket body, altogether the same effect as the insert 18 in FIG. 1. At the same time, friction with the metallic arch wire is approximately equally as low.

The inventive brackets described above may, of course, be bonded onto tapes and not only directly onto the tooth surface. The advantages of the inventive brackets as described do, of course, remain the same.

I claim:

1. An orthodontic aid for transferring tooth correcting forces supplied by an arch wire to a tooth comprising a substantially plastic body having a lower surface and an upper surface, the lower surface forming a base for bonding the plastic body to the tooth, the upper surface having a slot for receiving the arch wire and attachment means for holding the wire in the slot; and a reinforcement produced using a ceramic material and held in a force fit in the slot for increasing the mechanical strength of the plastic body where it is acted upon by the tooth correcting forces.

2. An orthodontic aid as defined in claim 1, wherein the ceramic material comprises an oxide ceramic material.

3. An orthodontic aid as defined in claim 1, wherein the ceramic material comprises sintered polycrystalline alumina.

4. An orthodontic aid as defined in claim 1, wherein the reinforcement comprises a plastic part containing particulate ceramic material.

5. An orthodontic aid as defined in claim 4, wherein the particulate ceramic material comprises zirconia.

6. An orthodontic aid as defined in claim 4, wherein the average particle size of the ceramic material is approximately 5 µm to 100 µm.

7. An orthodontic aid as defined in claim 4, wherein the particulate ceramic material comprises silicon dioxide.

8. An orthodontic aid as defined in claim 4, wherein the particulate ceramic material comprises alumina.

9. An orthodontic aid as defined in claim 1, wherein the reinforcement is disposed within the slot between the arch wire and the plastic body for transferring correction forces from the arch wire to the aid.

10. An orthodontic aid as defined in claim 1, wherein the reinforcement comprises a translucent material.

11. An orthodontic aid as defined in claim 1, wherein the plastic body comprises a polycarbonate resin.

12. An orthodontic aid as defined in claim 1, wherein the reinforcement strengthens the slot of the plastic body for interaction with the arch wire without altering the mechanical properties of the base.

13. An orthodontic aid as defined in claim 1, wherein the plastic body comprises a polyethylene resin.

14. An orthodontic aid as defined in claim 1, wherein the plastic body comprises a polyester resin.

15. An orthodontic aid as defined in claim 1, wherein the plastic body comprises a polyacrylic resin.

16. An orthodontic aid as defined in claim 1, wherein the plastic body comprises a copolymer derived from a combination of at least two of the group consisting of polycarbonate, polyethylene, polyester or polyacrylic resin.

* * * * *